United States Patent

Stasz

[11] Patent Number: 5,311,875
[45] Date of Patent: May 17, 1994

[54] BREATH SENSING APPARATUS

[76] Inventor: Peter Stasz, 8357 Eastwood Rd. NE., Moundsview, Minn. 55112

[21] Appl. No.: 977,486

[22] Filed: Nov. 17, 1992

[51] Int. Cl.$^5$ ............................................. A61B 5/087
[52] U.S. Cl. ........................................ 128/724; 128/716
[58] Field of Search ............... 128/716, 719, 724–725, 128/721, 671, 639–640, 736; 374/178, 183, 185; 338/308

[56] References Cited

U.S. PATENT DOCUMENTS

| | | |
|---|---|---|
| 4,960,118 | 10/1990 | Pennock . |
| 4,971,065 | 11/1990 | Pearce . |
| 4,989,612 | 2/1991 | Fiore ................................. 128/721 |
| 5,099,702 | 3/1992 | French ............................. 128/721 X |
| 5,161,541 | 11/1992 | Bowman et al. . |
| 5,201,322 | 4/1993 | Henry et al. ......................... 128/719 |

OTHER PUBLICATIONS

Atochem Sensors, Inc.—Technical Notes, Pennwalt Corp. ©1987, pp. 1–64.

Primary Examiner—Angela D. Sykes
Attorney, Agent, or Firm—Haugen and Nikolai

[57] ABSTRACT

A breathing sensor comprising a thin flexible compliant film transducer exhibiting piezoelectric and pyroelectric properties. The transducer preferably comprises a thin film of polyvinylidene fluoride (PVDF) having a pattern of metallization on the opposed surfaces thereof defining electrodes. The transducer is designed to be affixed proximate a person's airway such that the tidal flow of inspired and expired air will impinge upon the transducer. It is adapted to be coupled to electronic circuitry for indicating normal breathing, for providing an alarm in the event of sleep apnea and for providing an indication when sound related to respiratory distress is present.

10 Claims, 3 Drawing Sheets

BREATH SENSING APPARATUS

BACKGROUND OF THE INVENTION

I. Field of the Invention

This invention relates generally to monitoring devices for respiratory activity, and more particularly to a transducer which can be readily positioned relative to the respiratory passages of a subject for producing an electrical signal related to temperature changes due to impingement of inspired or expired air thereon and/or sound produced during breathing.

II. Discussion of the Prior Art

A variety of devices are described in the prior art for monitoring respiratory activity of a subject. For example, neonates who may have evidenced a propensity towards SIDS (sudden infant death syndrome) are provided with a breathing monitor which will provide an alarm in the event of sleep apnea. In this regard, reference is made to the Pearce U.S. Pat. No. 4,971,065. There is described a transducer for detecting apnea which comprises a deformable pad having a serpentine pattern of an electrically resistive material adhered to that pad, the material exhibiting a resistance change when deformed. The transducer would typically be placed on the crib mattress to detect even subdued breathing movements of that infant. The transducer is coupled to electrical circuitry for producing an alarm if the rhythmic breathing pattern ceases for more than a predetermined time.

The Pennock U.S. Pat. No. 4,960,118 describes a transducer arrangement in which piezoelectric devices are mounted on belts extending around the abdomen and thorax in such a way that the strain on the transducers due to expansion and contraction of the abdomen and thorax during breathing produces a detectable variation in an output signal.

The EdenTec Corporation of Eden Prairie, Minn., manufactures and sells an air flow sensor designed to be adhesively attached to a patient's upper lip so as to be exposed to the tidal flow of respiratory gases during inspiration and expiration. It is more particularly described in the Bowman et al. U.S. Pat. No. 5,161,541. The transducer comprises a substrate on which is deposited a thermistor, i.e., a material exhibiting a significant resistance change with changes in temperature. The device is adapted to be connected to a suitable electronics module for developing a detectable change in voltage as the resistance varies due to temperature changes occasioned by the impingement of respiratory gases onto the transducer during inspiration and expiration. Typically, resistive printed inks have a small temperature coefficient producing a very small change in resistance of about 0.05% with the typical 1° to 2° C. temperature change that occurs when breathing onto the sensor. This produces a very small signal voltage output of less than 100 microvolts with a typical adult patient. The signal is even less when the sensor is used with an infant because of the smaller volume of air exhaled.

The present invention overcomes this drawback by using a piezo material that has pyroelectric properties producing output voltages that are approximately 1,000 times greater than the resistive printed ink sensor. These larger signals make it easier to detect small changes of temperature.

SUMMARY OF THE INVENTION

To achieve the foregoing and other objects, and in accordance with the purposes of the present invention described herein, a novel breathing sensor is provided for detecting breathing or other respiratory abnormalities. It comprises a flexible, compliant film transducer exhibiting both piezoelectric and pyroelectric properties with the film transducer being shaped so as to allow it to be readily positioned relative to the respiratory passages of an animal or person to intercept the tidal flow of respiratory gases drawn into and exiting those passages. The transducer provides a low frequency output voltage signal proportional to change in temperature during the impingement of respiratory gases thereon as well as a relatively higher frequency output voltage which is proportional to sound level, such as may be produced during periods of respiratory distress or snoring episodes. This flexible, compliant piezoelectric and pyroelectric film transduce is connected to an electronic circuit including amplifying and filtering devices which may be designed to pass those frequencies of interest while significantly attenuating frequency components of the output voltage, which may be due to motion artifacts or other noise.

In accordance with one embodiment, the circuit is designed to provide a visual or audible indication when the transducer output voltage is above a prescribed amplitude. Also disclosed is a circuit arrangement which provides an alarm should the tidal flow of respiratory gases cease for more than a predetermined time interval. Other circuit means are disclosed which discriminate against the relatively low frequency output from the transducer due to temperature changes, while enhancing the output from the transducer due to the piezoelectric effect where sounds made during distressed breathing or snoring episodes create the alarm condition.

The flexible, compliant piezoelectric and pyroelectric film transducer is preferably a polyvinyl fluoride (PVDF) film layer having first and second major surfaces, each supporting metallic electrodes as well as conductors extending from those electrodes to a pair of terminals which are adapted to mate with the electronic circuitry. Such transducers can be mass-produced at relatively low cost using rotary dies for stamping out individual transducers of a desired shape from the PVDF film sheets.

Figure 1:
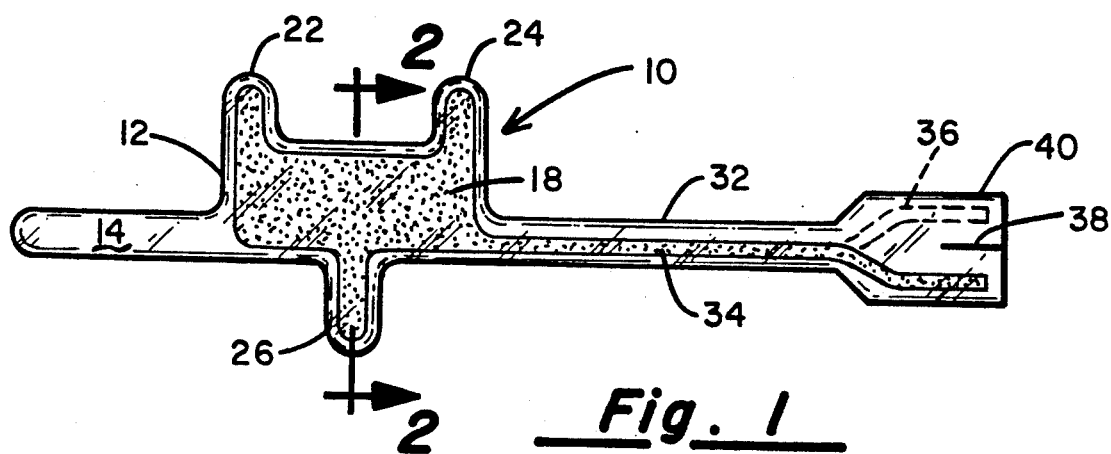
FIG. 1 is a plan view of the transducer portion of the breathing sensor of the present invention.
Figure 2:
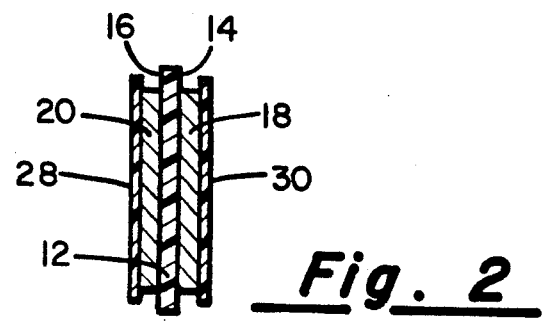
FIG. 2 is a cross sectional view taken along the line 2—2 in FIG. 1.

Referring first to FIG. 1, there is indicated generally by numeral 10 a transducer element constructed in accordance with the present invention. It comprises a thin plastic film 12 which preferably has a thickness in the range of from 0.5 to 20 mils and has opposed major surfaces 14 and 16 (FIG. 2). As those skilled in the art relating to dynamic film transducers understand, the film thickness is a parameter which is directly proportional to the output signal produced but inversely related to response time. The material from which the film member 12 is formed is preferably a material that exhibits both piezoelectric and pyroelectric properties. Typical of such films are those made from polyvinylidene fluoride (PVDF), that material being sold under the registered trademark, KYNAR, by the Pennwalt Corporation. This film material possesses dynamic characteristics. That is to say, it develops an electrical charge proportional to changes in mechanical stress or strain imposed on it. It also acts as a pyroelectric dynamic device developing an electrical charge proportional to temperature changes to which the film is exposed.

In creating a transducer, a thin, flexible, semi-transparent layer of metallization may be adhered to the opposed major surfaces 14 and 16 thereof, these metallization layers being identified by numerals 18 and 20 in FIG. 2. In that FIG. 1 is a plan view, only the metallization layer 18 on the major surface 14 is visible, it being understood that the opposite side 16 has a similar metallization pattern formed thereon.

With reference again to FIG. 1, the film layer 12 has integrally formed lobes 22 and 24, which are spaced apart by a distance corresponding to the lateral spacing between nares of the subject's nose. Likewise, a third lobe 26 is shown as projecting downward in a direction opposite from the lobes 22 and 24 and is generally centered therebetween so as to overlay the mouth of the subject on which the transducer is used. The zones of sensitivity of the transducer are those that include overlapping metallization on the opposed major surfaces. Thus, while the entire KYNAR film serves as a substrate, only those portions effectively sandwiched between the metalized electrodes contribute to the voltage developed due to temperature shifts or applied force changes.

Figure 3:
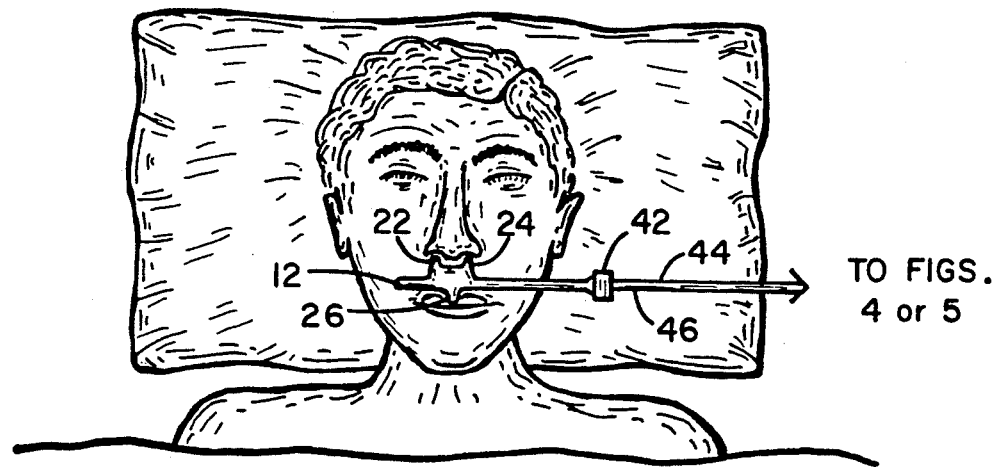
FIG. 3 illustrates the transducer of FIG. 1 placed on a human subject.

FIG. 3 illustrates the placement of the transducer device of FIG. 1. By utilizing a pressure-sensitive adhesive layer 28 on the undersurface of the transducer assembly, it may be adhered to the upper lip of a subject with the lobes 22 and 24 subtending the nasal openings or nares and with the lobe 26 overlaying the subject's mouth. A non-porous film layer 30 (FIG. 2) is adhered to the exposed surface of the metallization layer 18.

Referring to FIG. 1 again, the transducer includes an elongated tail segment 32 having the conductive strips 34 and 36 on opposed major surfaces thereof. A slit 38 is made through the thickness dimension of the film 12 to facilitate folding of the terminal portion 40. When so folded, the metallization on opposed sides of the strip will be aligned with one another but separated by a layer of insulation such that the folded end segments of the tail 32 can be readily inserted into an electrical connector 42 to mate With conventional wires 44 and 46 which lead to the electronic circuitry illustrated schematically in FIGS. 4 and 5.

Because the transducer made in accordance with the present invention is very flexible, affords a low profile and is light in weight, it is comfortable to wear. Moreover, it can be made in differing sizes to accommodate infants, children, adolescents and adults. Because the transducer can be made very economically, it can be used once and discarded. While the transducer of FIG. 1 is shown in FIG. 3 as being directly adhered to the upper lip of a patient, those skilled in the art can appreciate that transducers having a different shape configuration can be prepared in accordance with the teachings of the present invention and applied directly to the patient or to other respiratory performance related equipment, such as anesthesia masks, pneumotach mouthpieces, tracheotomy tubes, etc.

Figure 4:
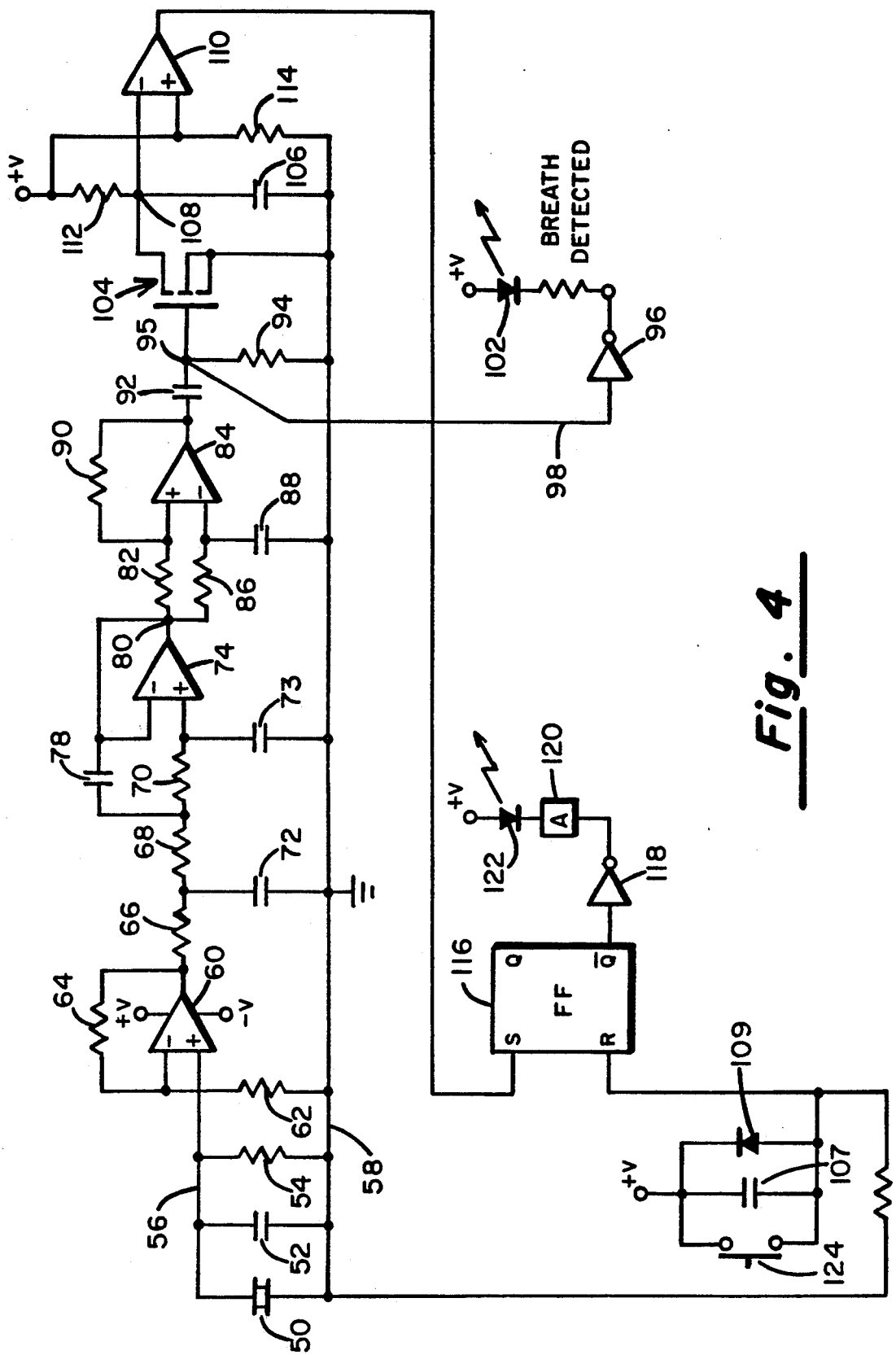
FIG. 4 is a schematic electrical circuit diagram of an alarm system responsive to the output of the transducer of FIG. 1 for producing an alarm should breathing cease for more than a predetermined time interval.

FIG. 4 is an electrical circuit schematic diagram depicting the manner in which the transducer of the present invention can be utilized in an apnea monitor. As will be explained in greater detail, this circuit operates to normally provide a visual indication so long as rhythmic breathing is occurring. Should an apnea episode occur which is longer than a preset time interval, the circuit operates to produce an alarm signal so that necessary intervention by a parent or other attendant can be had.

In the circuit of FIG. 4, the piezoelectric/pyroelectric transducer constructed in accordance with the present invention is identified by numeral 50. Connected in parallel with the transducer 50 is a capacitor 52 which functions to store the charge produced by the film transducer 50. A resistor 54 is also connected in parallel with the transducer between a conductor 56 and a ground rail 58. Conductor 56 is connected to the non-inverting input of an operational amplifier 60. A resistor 62 connects the inverting input of that amplifier to the ground rail. Connected between the output of the operational amplifier 60 and its inverting input terminal is a feedback resistor 64.

The output from the amplifier stage 60 is fed into a low-pass filter which is comprised of series-connected resistors 66, 68 and 70, a shunt capacitor 72 and an operational amplifier 74 having its non-inverting input connected to one terminal of the resistor 70 and its inverting input connected by a conductor 76 directly to its output. A capacitor 78 is connected between the remaining terminal of the resistor 70 and the inverting input of the operational amplifier 74. Another capacitor 72 is connected between the noninverting terminal of operational amplifier 74 and ground 58. The circuit components are such that the resistors 66, 68, 70, the operational amplifier 74 and the capacitors 72, 73 and 78 form a third order Butterworth low-pass filter, preferably having an upper cut-off frequency of about 5 Hz. In that normal rhythmic breathing is generally less than 5 Hz., the signals picked up by the transducer 50 related to such normal breathing will be amplified and passed through the filter while higher frequency signals due to motion artifacts or other noise sources will be attenuated.

The output from the low-pass filter appearing at junction 80 is applied to a self-referenced comparator stage which includes a resistor 82 connected between the output terminal 80 of the low-pass filter and the non-inverting input of operational amplifier 84. A resistor 86 is coupled between the terminal 80 and the inverting input of the op amp 84. A shunt capacitor 88 is tied between the inverting input of op amp 84 and the ground rail 58. A feedback resistor 90 couples the output of the op amp 84 back to its non-inverting input. The combination of the resistor 90 and the resistor 82 introduce hysteresis to the self-referenced comparator stage. Thus, the comparator produces a signal having a pulsatile waveform at its output. The pulse repetition frequency is dependent upon the frequency of respiration as detected by the transducer 50. A coupling capacitor 92 and a resistor 94 couple the pulsatile waveform to the input of the buffer inverter 96 by way of conductor 98. Each time the comparator stage outputs a pulse, the LED 102 turns on. Thus, regular breathing causes the LED 102 to blink on and off at a rate related to the breathing rate as detected by the transducer 50.

Connected to the junction 95 between the coupling capacitor 92 and the resistor 94 is a FET switch 104 and connected across the switch is a timing capacitor 106. The FET switch has its drain electrode connected to a junction point 108 and the capacitor 106 is connected between that junction and the ground rail 58. The junction 108 is connected to the inverting input of an operational amplifier 110 and to a source of positive potential, +V, via a resistor 112. That voltage source is also connected to the non-inverting input of the comparator 110 and a resistor 114 joins the non-inverting input to the ground rail.

The output from the comparator 110 is connected to the Set side of a flip-flop 116. It can be seen that as the charge on the timing capacitor 106 begins to build up by current flowing from the +V source through resistor 112, so long as breathing is occurring at a predetermined rate determined by the $R_{112} C_{106}$ time constant, the charge on the capacitor 106 will be shorted out by the FET switch 104 before the threshold for the comparator 110 is reached. Thus, the flip-flop 116 will remain reset causing the output from the inverter 118 to remain high, disabling the alarm 120 and preventing the alarm indicating LED 122 from glowing. If, however, breathing should cease so that the transducer 50 is no longer outputting its regular pulsatile waveform at a prescribed frequency, the switch 104 will remain off allowing the charge on capacitor 106 to build up to the point where it exceeds the threshold established for the comparator 110. This will result in a output from the comparator setting the flip-flop 116 which drives the inverted output from the flip-flop 116 high producing a low output from the inverter 118. This allows a current to flow from the voltage source, +V, through the LED 122 and the alarm 120 which signals the fact that breathing has ceased for at least a predetermined time interval determined by the resistor 112 and the capacitor 106.

Once appropriate action has been taken by the attendant, the alarm system may be reset by depressing the push-button 124 and thereby applying a high input signal to the reset terminal of the flip-flop 116, placing the system in a stand-by mode until a subsequent episode of respiratory apnea occurs.

During initial power-up, capacitor 107 produces a spike across resistor 115, resetting the flip-flop 116. Diode 109 helps discharge capacitor 107 during quick power on-off cycling.

Figure 5:
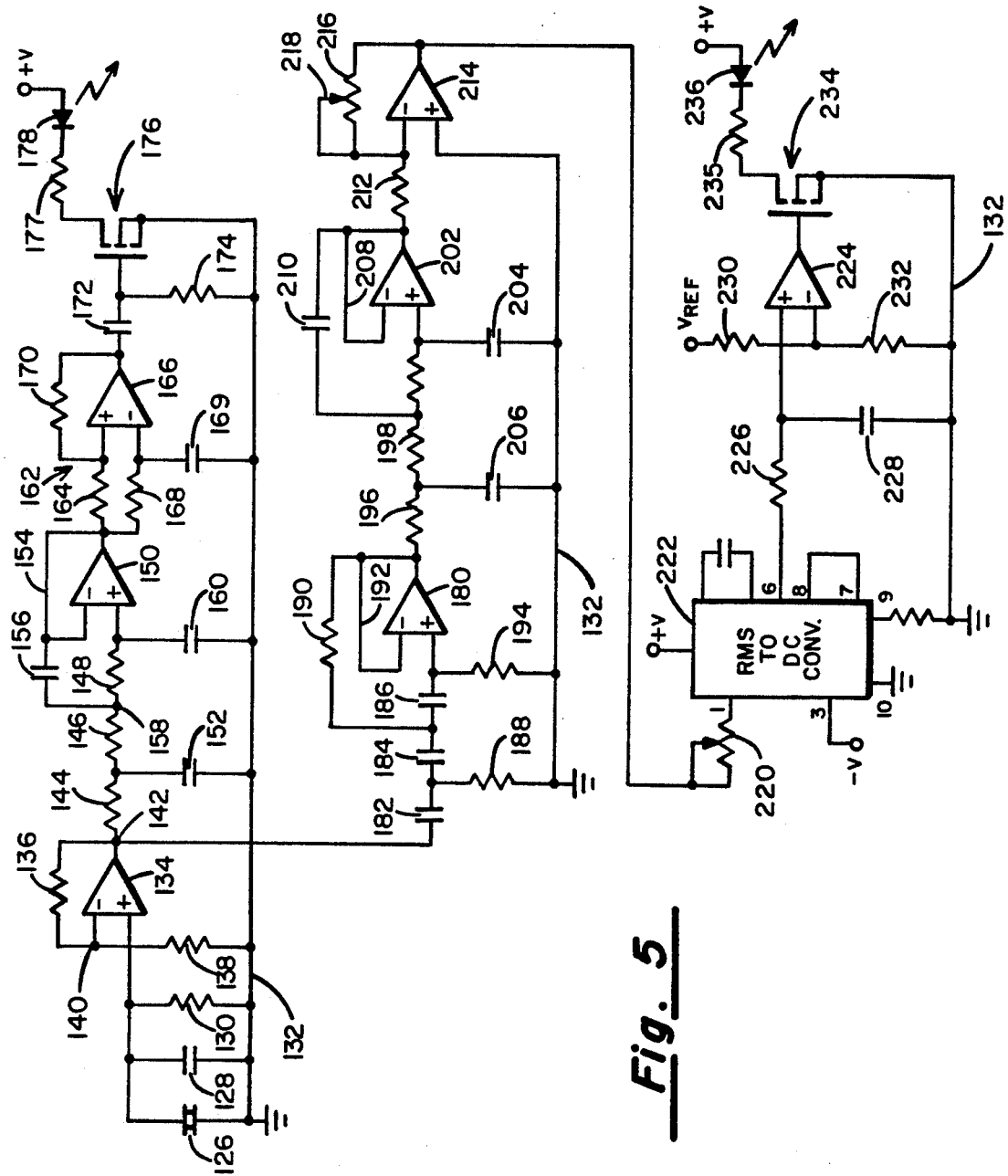
FIG. 5 is an electrical schematic circuit diagram of a circuit responsive to the output of the transducer of FIG. 1 and which provides an output during snoring episodes.

The circuit means of FIG. 4 is configured to take advantage only of the pyroelectric properties of the PVDF film transducer heretofore described. FIG. 5 illustrates by means of an electrical schematic the design of a circuit which takes advantage of both the pyroelectric and piezoelectric properties of the PVDF transducer heretofore described. In this figure, the transducer is identified by numeral 126 and, as in the earlier embodiment of FIG. 4, has a storage capacitor 128 connected directly in parallel with it to store the charge developed by the film transducer. Connected in parallel with the combination of the transducer and the storage capacitor is a resistor 130 of relatively large ohmic value. This parallel combination of components is connected between a ground rail 132 and the non-inverting input of an op amp 134 connected as an amplifier stage whose gain is determined by a feedback resistor 136 and a further resistor 138 The inverting input of the op amp 134 is connected to the junction point 140 between these two resistors.

The output from the amplifier stage 134 appearing at junction point 142 is fed into two channels. The first channel includes a low-pass filter stage and a detector stage and is similar to that previously illustrated in FIG. 4 for indicating that breathing is taking place. Here, it is the pyroelectric properties of the transducer that are exploited. The second channel is arranged to exploit the piezoelectric properties of the transducer.

Considering first the breath detect channel, it includes a low-pass third order Butterworth filter comprising resistors 144, 146 and 148 connected in series between the output terminal 142 of the amplifier stage 134 and the non-inverting input of a further operational amplifier 150. A shunt capacitor 152 is connected between the common terminal between the resistors 144 and 146 and the ground rail 132. The output from the op amp 150 is connected by a conductor 154 directly to the inverting input thereof and a capacitor 156 connects a junction point 158 between the series connected resistors 146 and 148 to the inverting input as well. A capacitor 160 connects the non-inverting input of the op amp 150 to the ground rail. The circuit components for the resistors 144, 146, 148 and capacitors 152, 156 and 160 create a low-pass filter characteristic having an upper cutoff frequency of about 5 Hz. Because the normal frequency of breathing is below this value, those components of the signal generated by the transducer 126 will be amplified and passed to the detector stage indicated generally by numeral 162 whereas higher frequency components of the output from the transducer will be attenuated.

The detector stage 162 includes a resistor 164 coupling the output from the filter stage to the non-inverting input of op amp 166 and a resistor 168 connecting the filter output to the inverting input of op amp 166. Capacitor 169 is connected between the non-inverting input of op-amp 166 and ground 132. A feedback resistor 170 is connected between the output from op amp 166 and its non-inverting input. As before, the feedback resistor 170 and the resistor 164 introduce hysteresis such that a pulsatile output is produced by the op amp 166 where the pulses are related to the cyclicly produced signals related to inhalation and exhalation. A coupling capacitor 172 and a resistor 174 feed the pulses to a FET switch 176 which drive it between a conducting and unconducting state. As a result, the LED 178 turns on and off in rhythm with the subject's breathing, thereby indicating that normal respiration is occurring. Resistor 177 limits the current through the FET.

The second channel includes a high-pass third order Butterworth filter comprised of an operational amplifier 180 along with series-connected capacitors 182, 184 and 186 connecting its non-inverting input to the junction point 142 at the output of the amplifier 134. A first resistor 188 is connected between the common junction of capacitors 182 and 184 to the ground rail 132. A feedback resistor 190 is connected between the output terminal of the op amp 180 and the common junction between the capacitors 184 and 186. The output is also directly connected by a conductor 192 to the non-inverting input. A resistor 194 is connected between the non-inverting input of op amp 180 and the ground rail 132. The output from the high-pass filter stage is fed into a low-pass filter stage which includes the series connected resistors 196, 198 and 200 leading to the non-inverting input of the operational amplifier 202. A capacitor 204 is connected between the non-inverting input of op amp 202 and the ground rail and, likewise, a capacitor 206 is connected between the common junction between resistors 196 and 198 and the ground rail 132. A conductor 208 directly connects the output of op amp 202 to the inverting input while a capacitor 210 connects the output of that amplifier to the common junction between resistors 198 and 200. The component values of the high-pass filter stage and the low-pass filter stage define a pass band for frequencies between about 150 Hz and about 500 Hz. It is in this range that sound waves impinging upon the transducer will produce electrical signals whose frequency components are due to the piezoelectric effect exhibited by the transducer 126. Thus, for example, sounds occasioned by snoring episodes would be expected to pass through the two filter stages in the sound channel whereas lower frequency components, due to the pyroelectric effect of breathing upon the transducer, are blocked from that second channel.

The output from the low-pass filter stage is coupled through a resistor 212 to an amplifier stage which includes the op amp 214 whose non-inverting input is tied directly to the ground rail. Its inverting input is joined to the resistor 212 and to a variable resistor 216 connected as a feedback element between the output of op amp 214 and its inverting input. By adjusting the position of the potentiometer wiper arm 218, the gain of the amplifier stage 214 can be adjusted.

The output from the amplifier stage 214 is then fed through another variable resistor 220 to a RMS to DC converter, an integrated circuit chip identified by numeral 222. The output from the converter 222 is then applied as an input to the non-inverting input of a op amp 224 configured as a comparator. An integrating circuit, including a resistor 226 and a capacitor 228, is interposed between the RMS to DC converter and the comparator 224 such that when the summed or integrated signals due to sound components exceed a threshold voltage applied to the inverting input of the comparator via resistors 230 and 232, the comparator will output a voltage pulse for turning on a FET switch 234. This completes a circuit from a source of positive voltage, +V, through a LED or other type of indicator 236, resistor 235 and the switch 234 to the ground rail 132. The LED 236 or other suitable alarm Will then be activated until such time as the integrated output from the RMS to DC converter 222 falls below the threshold established for the comparator 224.

It can be seen then that the electronic circuitry of FIG. 4 functions to provide a regularly occurring output from an indicator 102 so long as breathing is occurring in a normal fashion Should breathing cease for a predetermined time interval, an alarm 120 will sound. As regards FIG. 5, the circuit shown there also is capable of providing a visual or audible indication that normal breathing is occurring, but has the added capability of also signaling when sound emanating from the subject due to snoring or other respiratory distress events are occurring.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices For example, the transducer may have differing sizes and shapes to accommodate a variety of subjects or respiratory devices used with the subject. Hence, it is clear that various modifications, both as to the equipment details and operating procedures, can be accomplished without departing from the scope of the invention itself.

What is claimed is:

1. A breathing sensor comprising in combination:
   (a) a transducer adapted to be disposed relative to the respiratory passages of an animal or person to intercept the tidal flow of respiratory gases exiting said passages, said transducer comprising a flexible, compliant polyvinylidene fluoride (PVDF) film substrate exhibiting piezoelectric and pyroelectric properties, said film substrate having first and second major surfaces supporting electrodes having a pattern of flexible metallization thereon defining zones of sensitivity to thermal changes, said transducer producing a low frequency output voltage signal proportional to changes in temperature due to the impingement of respiratory gases thereon;
   (b) first and second flexible layers of insulation covering the flexible metallization on said first and second major surfaces; and
   (c) circuit means coupled to said electrodes for receiving said low frequency output voltage signal and producing one of a visual and audible indication when said output voltage signal is above a prescribed amplitude.

2. The breathing sensor as in claim 1 wherein said circuit means further provides an alarm when said tidal flow ceases for more than a predetermined time interval.

3. The breathing sensor as in claim 2 wherein said circuit means includes:
   (a) amplifier means operatively coupled to said electrodes for amplifying and shaping said output voltage signal;
   (b) low-pass filter means for attenuating a frequency component of said output voltage above a predetermined frequency related to expected breathing rate;
   (c) a comparator having an input connected to said low-pass filter means and an output, said output being of a first binary state when a signal on said input exceeds a predetermined threshold amplitude and a second binary state when said input is less than said predetermined threshold amplitude;
   (d) timing means connected to said output of said comparator, said timing means being reset periodically each time said output of said comparator is of said first binary state; and
   (e) alarm means coupled to said timing means for providing one of a visual and audible indication if said timing means is to reset within a predetermined time interval.

4. The breathing sensor as in claim 1 wherein one of said first and second insulating layers includes a pressure-sensitive adhesive thereon.

5. The breathing sensor as in claim 1 wherein the thickness of said PVDF film layer is in the range of from 0.5 to 20 mils.

6. The breathing sensor as in claim 5 wherein said film layer comprises an elongated strip having a pair of lobes projecting therefrom to underlay the person's nares and a further lobe projecting therefrom to overlay the person's mouth when said strip is adhered to a person's upper lip, at least said lobes including a portion of said pattern of metallization on opposed major surfaces thereof.

7. The breathing sensor as in claim 6 wherein said elongated strip includes first and second terminal portions individually connected to said pattern of flexible metallization on said first and second major surfaces.

8. The breathing sensor as in claim 1 wherein said transducer further produces an output voltage proportional to a sound level produced during snoring episodes.

9. The breathing sensor as in claim 8 wherein said circuit means further includes:

(a) amplifier means coupled to said transducer for amplifying variations in the output voltage signal from said transducer;

(b) band-pass filter means having an input and an output, said input being coupled to receive an output of said amplifier means and a pass band corresponding to predominant frequencies of sounds made during snoring episodes; and (c) means coupled to the output of said band-pass filter for indicating when snoring episodes are in progress.

10. The breathing sensor as in claim 8 wherein the frequency of said output voltage proportional to a sound level is higher than said low frequency output voltage signal proportional to changes in temperature.

* * * * *